United States Patent [19]
Cavazza

[11] Patent Number: 5,998,474
[45] Date of Patent: Dec. 7, 1999

[54] L-CARNITINE OR DERIVATIVES THEREOF AND ANTIOXIDANTS FOR THE PREVENTION AND TREATMENT OF DISEASES ELICITED BY OXIDATIVE STRESS TO THE NERVOUS AND CARDIOVASCULAR SYSTEM

[75] Inventor: Claudio Cavazza, Rome, Italy

[73] Assignee: Sigma-Tau Industrie Farmaceutiche Riunite S.p.A., Italy

[21] Appl. No.: 08/819,262

[22] Filed: Mar. 18, 1997

[30] Foreign Application Priority Data

Mar. 29, 1996 [IT] Italy ................................. RM96A0199

[51] Int. Cl.⁶ .................................................. A61K 31/205
[52] U.S. Cl. .......................... 514/556; 514/474; 514/458; 514/562; 514/725; 424/702
[58] Field of Search ............................ 424/702; 514/562, 514/556, 458, 474, 725

[56] References Cited

U.S. PATENT DOCUMENTS 5,397,786   3/1995   Simone .................................... 514/300

OTHER PUBLICATIONS

Shigenaga et al., Proc. Natl. Acad. Sci. (91), pp. 10771–10778, Nov. 1994.

Monti et al., Am. J. Clin. Nutr. (55), pp. 1208S–1214S, 1992.

*Primary Examiner*—Phyllis G. Spivack

[57] ABSTRACT

Therapeutic use is described of L-carnitine, alkanoyl L-carnitines and pharmacologically acceptable salts thereof, in combination with hydrophilic antioxidants or lipophilic antioxidants for the prevention or treatment of a disturbance or disease elicited by oxidative stress.

16 Claims, 3 Drawing Sheets

L-CARNITINE OR DERIVATIVES THEREOF AND ANTIOXIDANTS FOR THE PREVENTION AND TREATMENT OF DISEASES ELICITED BY OXIDATIVE STRESS TO THE NERVOUS AND CARDIOVASCULAR SYSTEM

The present invention relates to a novel therapeutic use of L-carnitine, some alkanoyl L-carnitines and the pharmacologically acceptable salts thereof for the prevention and treatment of disturbances and diseases elicited by the oxidative stress brought about by oxygen free radicals.

More specifically, the present invention relates to the coordinated use of L-carnitine or an alkanoyl L-carnitine or the pharmacologically acceptable salts thereof with natural lipophilic antioxidants such as vitamin E or vitamin A and/or natural hydrophilic antioxidants such as vitamin C, glutathione (GSH) or selenium.

Several therapeutic uses of both L-carnitine and alkanoyl L-carnitine are already known, none of which is related to the use disclosed herein.

According to the present invention, by "co-ordinated use" of the aforesaid compounds, is meant indifferently either the co-administration, i.e., the substantially concomitant supplementation of L-carnitine, alkanoyl L-carnitine or a pharmacologically acceptable salt thereof and a natural lipophilic antioxidant such as vitamin E or vitamin A, or a natural hydrophilic antioxidant such as vitamin C, GSH or selenium, or the administration of a combination preparation or admixture of the aforesaid active ingredients, in addition to suitable excipients, if any.

Therefore, the present invention also relates to orally, parenterally, rectally or transdermally administrable pharmaceutical compositions suitable for treating disorders and pathologies related to the oxidative stress to body proteins and fatty acids which comprise, as active ingredients, L-carnitine, an alkanoyl L-carnitine or a pharmacologically acceptable salt thereof and a natural lipophilic antioxidant such as vitamin E or vitamin A and/or a natural hydrophilic antioxidant such as vitamin C, GSH or selenium.

The disturbances and diseases associated with protein oxidation include central nervous system diseases such as parkinsonism, trauma, cerebral palsy, diabetic neuropathy and ageing; peripheral nervous system diseases such as diabetic peripheral neuropathy and traumatic nerve damage; diseases of the cardiovascular system such as intermittent claudication, ischemic-reperfuson damage and stroke; and immune system abnormalities in conditions of low oxygen tension.

Though it has long been postulated that the formation of free radicals is the probable cause of ischemic damage, it has proved hard to demonstrate directly that such formation occurred and/or that it was sufficiently pronounced to overcome the antioxidative defences of the tissues, as reported by Curran et al., *Mol. Cell. Biol.* 5, 167–172, 1985.

In many cases the oxygenated tissues undergo damage, which may even be permanent, if they become ischemic and are then reperfused.

Molecular oxygen reduction products (MORP) are regarded as being responsible for cell damage in the course of ischemia and postischemic reperfusion of organs such as the brain, heart, intestines and kidneys, Braughler, J. M. and Hall, E. D. (1989) *Free Rad. Biol. Med.* 6, 289–301.

Moreover, in inflammation, aging and other important biological processes MORP are known to be mediators and/or modulators of various cell responses, Turner, E. et al., (1988) *Science* 242, 939–941.

Several therapeutic protocols have been developed aimed mainly at eliminating the toxic effect of MORP on target biological structures such as the cell membrane. The most commonly adopted approach has been to use molecules which mimic the well-known antioxidant action of natural compounds, which constitute part of the so-called primary antioxidant front, Bolli, R. (1989) *J. Am. Coll. Cardiol.* 12, 239–249. The most commonly used substances are, for example, superoxide dismutase, an enzyme capable of specifically removing the superoxide anion, and vitamin E, a molecule belonging to the tocopherol family capable of interrupting dangerous oxidative reactions affecting polyunsaturated fatty acids. Recent years have witnessed the marketing of OTC products, in which various combinations of non-enzymatic antioxidants (vitamin E, vitamin A, vitamin C, selenium, glutathione, etc.) are present. Clearly, this type of approach tends exclusively towards the removal of MORP or of other reactive molecules which are produced by the interaction of MORP with macromolecules of biological interest. This strategy takes no account of those biological abnormalities which set in even when it proves possible to reduce the original toxic potential of MORP. Furthermore, pathological events of unpredictable onset, such as organ ischaemia, often do not allow effective therapeutic intervention designed to cope with the antioxidant action of MORP. Thus, it is necessary to sensitize and/or potentiate the cell repair mechanisms in order to minimize the toxic effects due to the damaging action of MORP.

The exclusion of a direct antioxidizing action, i.e., of the primary type, of L-carnitine and its esters against MORP has already been abundantly demonstrated Arduini, A., et al. (1990) *Free Rad. Res. Commun.* 10, 325–332.

The typical target of MORP in the course of oxidative stress is the plasma membrane, whose integrity is essential for cell survival. The polyunsaturated fatty acids of membrane phospholipids are particularly sensitive to the oxidizing action of MORP. These fatty acids are capable of propagating the peroxidative reactions triggered by MORP, thus stabilizing the intermediate radical species Mead, J. F. (1976) in "*Free Radicals in Biology*" (Pryor W. A. ed.) Vol. 1 pp. 51–80, Academic Press, New York. The peroxidation of the biological membranes may generate various oxidation products which cause significant alterations of membrane structure and function Arduini, A. et al. (1989) *Arch. Biochem. Biophys.*, 273, 112–119.

The invention described herein is based on the surprising synergistic effect occurring between L-carnitine, or an alkanoyl L-carnitine (as it will be specified hereinbelow) or a pharmacologically acceptable salt thereof and a lipophilic natural antioxidant such as vitamin E or vitamin A and/or a hydrophilic natural antioxidant such as vitamin C, GSH or selenium. This synergistic effect is particularly surprising on account of the above-mentioned lack of direct antioxidizing action of L-carnitine and its aforesaid derivatives.

It has now been found that the coordinated use of L-carnitine, an alkanoyl L-carnitines or the pharmacologically acceptable salts thereof and the aforesaid antioxidant agents, whilst eliminating the toxic effect elicited by MORP's against the targeted biological structures of cells, not only prevents cell damage but also enhances the process of cell repair, thus allowing remarkable therapeutic results to be achieved.

The alkanoyl L-carnitines useful for the novel therapeutic use of the present invention are those wherein the alkanoyl group is a straight or branched group having from 2 to 8, preferably from 2 to 6 carbon atoms.

Particularly preferred are acetyl, propionyl, butyryl, valeryl and isovaleryl L-carnitine.

Pharmaceutically acceptable salts of carnitine or alkanoyl L-carnitine include, in addition to the inner salts, all the pharmaceutically acceptable salts which are prepared by the addition of an acid to L-carnitine, respectively, and which do not give rise to undesirable toxic or side effects.

The formation of pharmaceutically acceptable acid addition salts is well known to the experts in pharmacy and pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulphate, glucose phosphate, tartrate and acid tartrate salts.

For the sake of simplicity and clarity, hereinbelow reference will be made to L-carnitine only, it being understood, however, that whatever disclosed in connection with L-carnitine equally applies to the above-identified alkanoyl L-carnitines and pharmacologically acceptable salts thereof.

The compositions of the present invention prove particularly effective in inhibiting the toxic effect of MORP by acting both as primary and secondary antioxidants with the result that they can be used in the pharmaceutical field for the prevention or treatment of central nervous system diseases such as parkinsonism, cerebral palsy and diabetic neuropathy; peripheral nervous system diseases such as diabetic peripheral neuropathy and traumatic nerve damage; diseases of the cardiovascular system such as stroke, ischemia-reperfusion damage and intermittent claudication; and damage to the immune system in conditions of low oxygen tension.

The efficacy of the co-ordinated use according to the invention has been confirmed by various pharmacological tests, some of which are reported here below.

PHARMACOLOGICAL TESTS

I) Index of oxidative damage by evaluation of thiobarbituric acid reaction products (TBARS) produced by erythrocytes Animal treatment For this study 20 male Wistar rats aged 3 months were used. All animals were treated with a mixture of primary antioxidants (vitamin E 200 UI/kg and ascorbic acid 30 mg/kg) administered orally for 30 consecutive days. In a subgroup of 10 rats oral L-carnitine (50 mg/kg) was added to the basic treatment. The study was conducted according to the "open" experimental design and the choice of the subgroup of animals receiving combined antioxidant plus L-carnitine treatment was done using a random method.

Red blood cell preparation

At the end of the treatment, venous blood samples were taken in test tubes containing heparin. Leukocytes and platelets were removed via a chromatographic column containing cellulose and alpha-cellulose (1:1 w/w). The red blood cells were then washed three times with saline solution.

Incubation conditions

All incubations were done in an oscillating bath at 37° C. For experiments with intact cells, the red blood cells were washed one last time with Krebs incubation buffer (NaCl 120 mM; KCl 5 mM; $MgSO_4$ 1 mM; $NaH_2PO_4$ 1 mM; sucrose 40 mM; glucose 5 mM; Tris-HCl 10 mM; pH 7.4) and resuspended in the same buffer at a hematocrit of 5%. The erythrocytes were treated with ter-butyl hydroperoxide (t-BOOH), a chemical agent capable of generating lipoperoxidative phenomena in the erythrocyte membrane, at a concentration of 2 mM. At the end of the treatment with t-BOOH, the erythrocytes were washed three times with incubation buffer. All washings were done at 4° C.

Determination of the oxidative damage index

The oxidative damage index chosen was the thiobarbituric acid reaction product (TBARS) index. For the determination and quantification of TBARS produced by the erythrocytes the method described by Tsun-Yee Chiu and Claster *Methods in Haematology* Vol. 19, pp. 203–236. Churchill Livingstone, N.Y. was used.

The results are presented in FIG. 1.

II) Index of oxidative stress by evaluation of the phosphatidylethanolamine/sphingomyelin ratio Animals were treated and red blood cells prepared as in the previous test. The incubation conditions were also identical to those used in the previous test.

Extraction and separation of phospholipids

The lipid components of the erythrocyte membrane were extracted according to the method described by Rose and Oklander Rose, H. G. and Oklander, M. *J. Lipid Res.* (1965) 6: 428–431. To prevent oxidative phenomena butylhydroxytoluene (BHP 0.1%) was added to the extraction solvents. The lipid extract was dried under nitrogen flow and resuspended with toluene. For the separation of the individual phospholipid classes two-dimensional thin-layer chromatography was used Rouser, G. et al., *Lipids* (1970) 5: 494–496. The phospholipid classes were highlighted with iodine vapours. The individual phospholipid classes were identified by means cf the use of standards. Determination of the phosphorus present in the individual phospholipid classes was done according to Bottcher Bottcher, C. J. F. et al., *Anal. Chim. Acta* (1961) 24: 203–208.

The results are presented in FIG. 2.

III) Hemolysis in the course of oxidative stress

Animals were treated and red blood cells prepared as in the previous test. The incubation conditions were also identical to those used in the previous test.

Determination of hemolysis

Erythrocyte hemolysis was evaluated by measuring the amount of hemoglobin in the course of incubation with the oxidizing agent.

At the end of incubation, the erythrocytes were centrifuged and the buffs coat was used for the determination of hemoglobin released in the course of oxidative stress.

The hemoglobin determination was done spectrophotometrically according to the method described by Winterboum C., *Handbook of Methods for Oxygen Radical Research* (ed. R. Greenwad) pp. 13–41, CRC Press, Boca Raton, 1985.

The results are presented in FIG. III.

The addition of L-carnitine to the antioxidant mixture significantly reduces oxidative damage to the cell membrane. The quantity of TBARS was significantly reduced in erythrocytes obtained from the rats treated with L-carnitine and antioxidants compared to those treated with antioxidants alone (FIG. 1). Following oxidative stress, the phosphatidylethanolamine/sphingomyelin ratio of the erythrocytes of animals treated with antioxidants alone was reduced to a greater extent than that of erythrocytes treated with antioxidants plus L-carnitine (FIG. 2). Finally, hemolysis measured in the course of oxidative stress was significantly increased in the erythrocytes of animals treated with antioxidants alone compared to those treated with antioxidants plus L-carnitine (FIG. 3).

An appropriate pharmaceutical composition in unit dosage form comprises approximately 0.3 to approximately 0.5 g of L-carnitine or an equivalent amount of alkanoyl L-carnitine or their pharmacologically acceptable salts and approximately 50 to approximately 2000 U/I or, preferably, approximately 300 to approximately 1000 U/I of vitamin E and/or approximately 50 to approximately 500 mg or, preferably, approximately 100 to approximately 300 mg of vitamin C.

Figure 1:
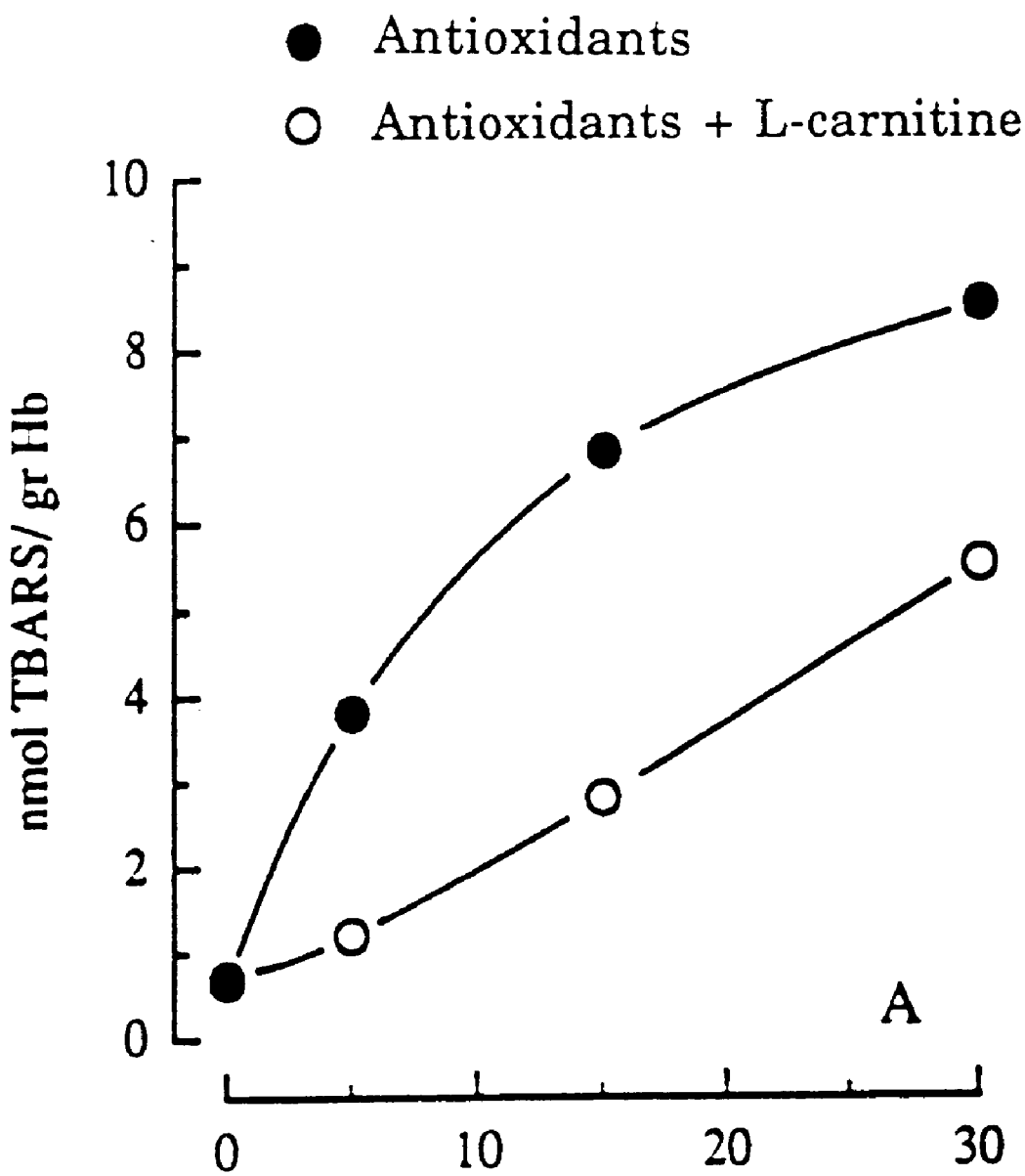
FIG. 1 shows that the quantity of TBARS was significantly reduced in erythrocytes obtained from the rats treated with L-carnitine and antioxidants compared to those treated with antioxidants alone.
Figure 2:
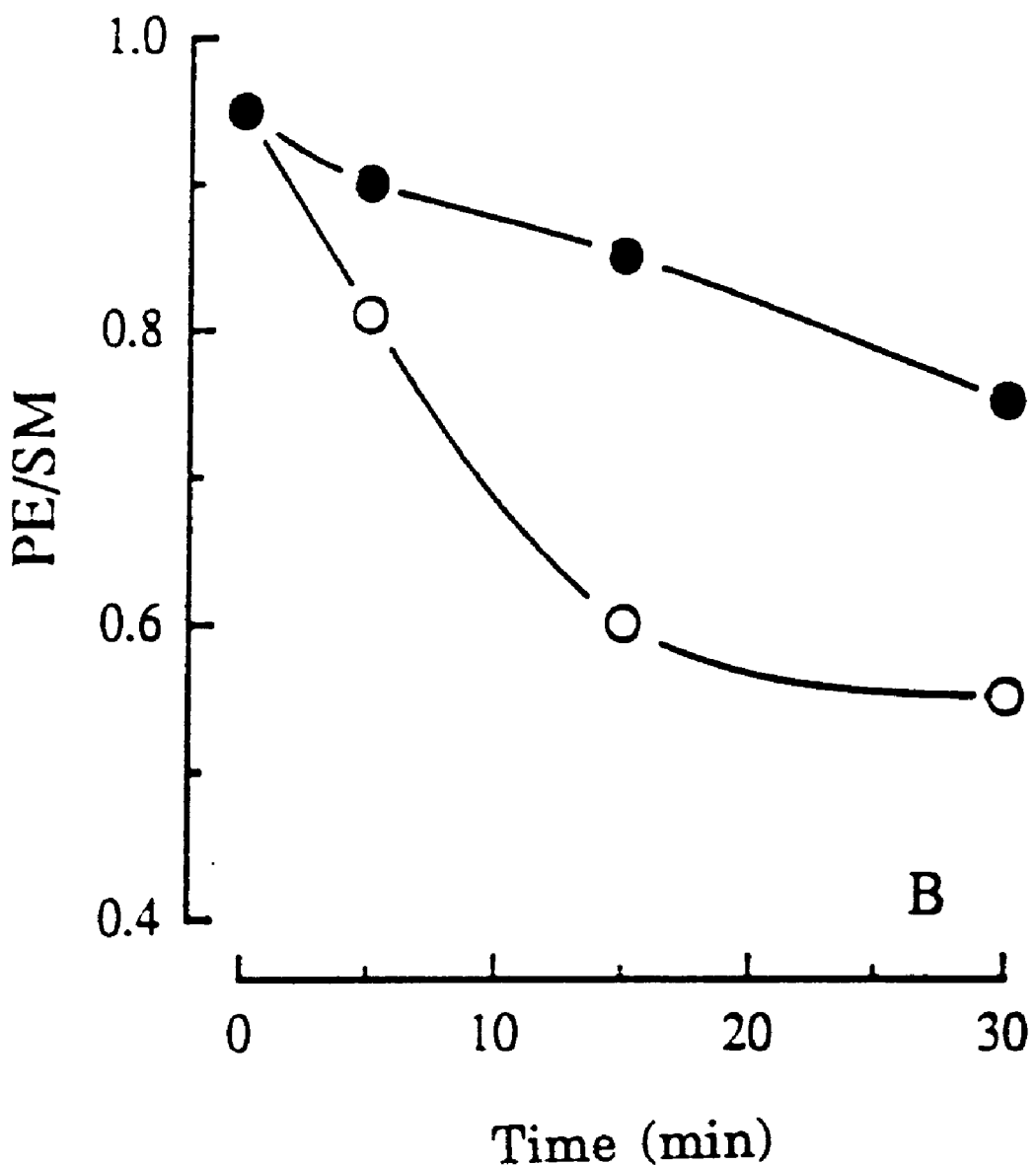
FIG. 2 shows that following oxidative stress, the phosphatidylethanolamine/sphingomyelin ratio of the erythrocytes of animals treated with antioxidants alone was reduced to a greater extent than that of erythrocytes treated with antioxidants plus L-carnitine.
Figure 3:
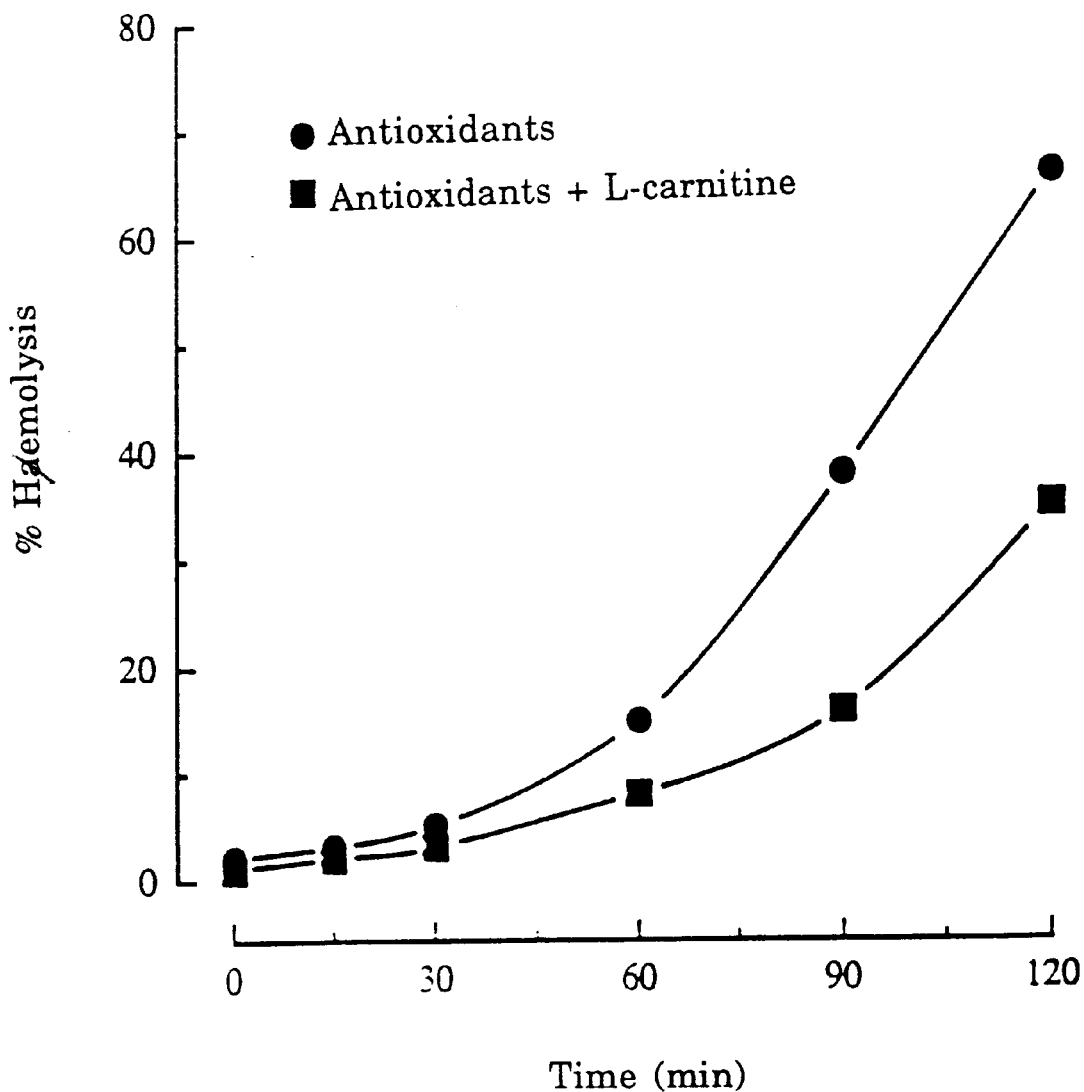
FIG. 3 shows haemolysis measured in the course of oxidative stress was significantly increased in the erythrocytes of animals treated with antioxidants alone compared to those treated with antioxidants plus L-carnitine.

The following non-limiting examples show some compositions according to the present invention.

EXAMPLES

1) L-carnitine mg 500; Vit. E U/I 1000; Vit. C mg 300
2) acetyl L-carnitine mg 500; Vit. E U/I 1000; Vit. C mg 300
3) propionyl L-carnitine mg 500; Vit. E U/I 1000; Vit. C mg 300
4) isovaleryl L-carnitine mg 500; Vit. E U/I 1000; Vit. C mg 300
5) valeryl L-carnitine mg 500; Vit. E U/I 1000; Vit. C mg 300
6) butyryl-L-carnitine mg 500; Vit. E U/I 1000; Vit. C mg 300
7) L-carnitine mg 500; Vit. A mg 1000; Vit C. mg. 300
8) acetyl L-carnitine mg 500; Vit. A mg 1000; Vit C. mg. 300
9) propionyl L-carnitine mg 500; Vit. A mg 1000; Vit C. mg. 300
10) isovaleryl L-carnitine mg 500; Vit. A mg 1000; Vit C. mg. 300
11) valeryl L-carnitine mg 500; Vit. A mg 1000; Vit C. mg. 300
12) butyryl L-carnitine mg 500; Vit. A mg 1000; Vit C. mg. 300
13) L-carnitine mg 500; Vit. E U/I 1000; GSH mg 500
14) L-carnitine mg 500; Vit. E U/I 1000; Vit C. mg. 300; GSH mg 500
15) L-carnitine mg 500; Vit. A mg 100; Vit. C mg 300, selenium mg 40.

I claim:

1. A composition for the prevention or treatment of a disturbance or disease elicited by the oxidative stress brought about by oxygen free radicals consisting of an L-carnitne or an alkanoyl L-carnitine or the pharmacologically acceptable salts there of wherein the alkanoyl group, straight or branched, has 2–6 carbon atoms in combination and admixture with, independently, a lipophilic or hydrophilic antioxidant.

2. A composition of claim 1 wherein the alkanoyl L-carnitine is selected from the group consisting of acetyl-, propionyl-, butyryl, valeryl and isovaleryl L-carnitine.

3. A composition of claim 1 wherein the lipophilic antioxidant is vitamin E or vitamin A.

4. A composition of claim 1 wherein the hydrophilic antioxidant is selected from the group consisting of vitamin C, glutathione (GSH) and selenium.

5. An orally, patenterally, rectally or transdermally administrable pharmaceutical composition for the prevention or treatment of a disturbance or disease elicited by the oxidative stress brought about by oxygen free radicals consisting of L-carnitine or an alkanoyl L-carnitine wherein the alkanoyl group, straight or branched, has 2–6 carbon atoms or the pharmacologically acceptable salts thereof in combination and admixture with, independently, a lipophilic or a hydrophilic antioxidant, and a pharmacologically acceptable excipient thereof.

6. A composition of claim 5 wherein the alkanoyl L-carnitine is selected from the group consisting of acetyl-, propionyl-, butyryl, valeryl and isovaleryl L-carnitine.

7. A composition of claim 5 or 6 wherein the lipophilic antioxidant is vitamin E or vitamin A.

8. The composition of claim 7 in unit dosage form comprising 0.3–0.5 g of L-carnitine or an alkanoyl L-carnitine and 50–20,000 U/I of vitamin E.

9. A composition of claim 8 comprising 300–1000 U/I of vitamin E.

10. A composition of claim 5 or 6 wherein the hydrophilic antioxidant is selected from the group consisting of vitamin C, glutathione (GSH) and selenium.

11. A composition of claim 10 in unit dosage form comprising 300–500 mg of vitamin C and 0.3–0.5 g of L-carnitine or an alkanoyl L-carnitine.

12. A method of preventing or treating a disturbance or disease related to oxidative stress brought about by oxygen free radicals comprising administrating to a patient an L-carnitine or alkanoyl L-carnitine or a phanmacologically acceptable salts thereof wherein the alkanoyl group is straight or branched and has 2–6 carbon atoms in combination and admixture with, independently, a lipophilic or hydrophilic antioxidant.

13. A method of claim 12 wherein the disturbance and disease is selected from the group consisting of a central nervous system disease, a peripheral nervous system diseases, a disease of the cardiovascular system, and an immune system abnormality.

14. A method of claim 12 wherein the alkanoyl L-carnitine is selected from the group consisting of acetyl-, propionyl-, butyryl-, valeryl and isovaleryl L-carnitine.

15. A method of claim 12 wherein the lipophilic antioxidant is vitamin E or vitamin A.

16. A method of claim 12 wherein the hydrophilic antioxidant is selected from the group consisting of vitamin C, glutathione (GSH) and selenium.

* * * * *